United States Patent

Hansen et al.

[11] Patent Number: 6,140,548
[45] Date of Patent: Oct. 31, 2000

[54] TAB MEMBER

[75] Inventors: Grazyna Hansen, Farum; Hanne Jensen, Koebenhavn, both of Denmark

[73] Assignee: Coloplast A/S, Humlebaek, Denmark

[21] Appl. No.: 09/117,946

[22] PCT Filed: Feb. 7, 1997

[86] PCT No.: PCT/DK97/00048

§ 371 Date: Aug. 10, 1998

§ 102(e) Date: Aug. 10, 1998

[87] PCT Pub. No.: WO97/28771

PCT Pub. Date: Aug. 14, 1997

[30] Foreign Application Priority Data

Feb. 9, 1996 [DK] Denmark .................. 0134/96

[51] Int. Cl.[7] ...................................... A61F 13/00
[52] U.S. Cl. ................................................ 602/57
[58] Field of Search ................. 602/57–59, 41–56, 602/900, 903, 904; 206/440, 441; D24/189

[56] References Cited

U.S. PATENT DOCUMENTS

| | | |
|---|---|---|
| 4,646,731 | 3/1987 | Brower . |
| 4,744,355 | 5/1988 | Faasse, Jr. . |
| 4,753,232 | 6/1988 | Ward . |
| 5,106,629 | 4/1992 | Cartmell et al. .................. 424/445 |

FOREIGN PATENT DOCUMENTS

| | | |
|---|---|---|
| 0 168 174 | 1/1984 | European Pat. Off. . |
| 0 630 629 | 12/1994 | European Pat. Off. . |
| 2128479 | 5/1984 | United Kingdom . |
| 2224445 | 5/1990 | United Kingdom . |
| WO94/14393 | 7/1994 | WIPO . |

Primary Examiner—Kim M. Lee
Attorney, Agent, or Firm—Jacobson, Price, Holman & Stern, PLLC

[57] ABSTRACT

A tab member (25), especially for use as a "non-touch" grip for applying a dressing (21) comprising an adhesive layer (23) and optionally a release line (24) to the skin without touching the adhesive layer (23). The tab member (25) comprises at least a first flap member (26) and a second flap member (27) being joined along one edge thereof so as to form a tab having a V-formed cross section substantially perpendicular to the line of conjunction. The combined thickness of the two flap members (26, 27) in the area of conjunction (28) is smaller than the thickness of a bent edge of the two flap members (26,27). This is a particular advantage while a decrease of the thickness of the area of conjunction (28) results in a decrease in the area of the adhesive (23) in front of the area of bending or conjunction (28), which may be subjected to air.

17 Claims, 4 Drawing Sheets

TAB MEMBER

BACKGROUND OF THE INVENTION

1. Field of the Invention

The present invention relates to a tab member especially for use as a "nontouch" grip for applying a dressing comprising an adhesive layer and optionally a release liner to the skin without touching the adhesive layer, a method for manufacturing such tab member and a dressing comprising the tab member.

2. Description of Related Art

As it is commonly known thin wound dressings are difficult to apply to wounds, especially in curved areas, without wrinkling or sticking to themselves or to the users, e.g., a nurse or assisting persons fingers. It is desirable to apply all kinds of dressings without touching the adhesive layer in order to avoid reducing the adhesiveness. Because of the risk of introducing bacteria to the wound it is desirable to apply a dressing to a patient's skin without touching the surface of the dressing that is to come into contact with the skin. The prior art discloses several methods for facilitating handling of a wound dressing.

GB Patent APPLICATION 2,128,479 describes a surgical dressing having two release sheets, each covering half of the dressing and having a free edge curved at the center of the dressing. As the curved edges of the release sheets are peeled back, the center of the dressing is applied over a catheter or to a wound, followed by the ends, thereby preserving sterility by eliminating the need to touch the adhesive surface of the dressing.

U.S Pat. No. 4,753,232 discloses a "handle" portion along one edge of the dressing. After the dressing is applied, the handle may be removed by tearing, or it may carry an adhesive coating so that it may be adhered to the skin of the patient.

Another known method of avoiding contact with the edges of a bandage by fingers or forceps is disclosed in U.S. Pat. No. 4,646,731 disclosing a bandage which is coated with an adhesive and the edges of which are protected by a pair of folded V-shaped tabs. After removing the backing sheet from the bandage, one tab is removed and the corresponding end of the bandage is applied to the skin. The second tab is grasped and removed as the entire length of the bandage is then applied.

European Patent Application No. EP 0 168 174 discloses a dressing comprising a first adhesive contact layer and an inner surface of a thin film backing. A release layer covering the first adhesive layer is removed prior to application of the dressing, and the film backing preferable has an edge portion free of adhesive to facilitate the removal of the release layer from the dressing without touch conlaminating the underside of the dressing. A relatively rigid carrier section is secured to the outer surface of the film backing by a second adhesive layer, and the carrier section includes rigid handles keeping the dressing extended during application of the dressing to a skin surface and prevents the dressing from curling or folding up.

U.S. Pat. No. 4,744,355 discloses a solution to a problem associated with excessive peeling force during removal of backings from wound dressings by dividing the release liner in halves. A wound dressing is disclosed in which the release liner halves are each divided into a release liner main body and a release liner edge strip. The release liner main body overlaps a portion of the edge strip and the two are secured to each other by a flexible hinge. As the release liners are pulled away from the wound dressing, the hinge means are employed, thus reducing the peeling force.

U.S. Pat. No. 5,106,629 discloses a dressing having a thin transparent film layer, a stable backing layer over the outer surface of the transparent layer, and a release liner. The backing layer and the release liner each have a corner tab to facilitate the peeling of each from the transparent layer.

Published EP APPLICATION No. EP 0 630 629 discloses a flexible wound dressing product that includes a thin-film layer, an adhesive layer, a backing layer which may be porous, an optional support layer, an optional release liner, and a hydrogel material without the use of an adhesive. The wound dressing may also include a removable V-shaped tab interposed between the thin film layer and release liner, providing a grippable surface for the removal of the release liner from the transparent thin film layer and to facilitate the handling of said wound dressing during application of the dressing to the wound.

GB Patent Application, No. 2 224 445 A discloses an adhesive dressing which comprises a backing layer having a pressure sensitive adhesive layer over one surface thereof, a removable protector which covers the adhesive layer and extends beyond the backing layer at one or more edges and a conformable support layer which is reversibly attached to the non-adhesive surface of the backing layer and extends beyond the backing layer at one or more of the edges. Said protector comprises first and second parts, the first part having a portion extending away from the adhesive surface and bent back to form a V-shape and the second part having a portion extending away from the adhesive surface and overlying the V-shaped first part.

Published International Application No. WO 94/14393 discloses an adhesive dressing comprising a backing layer, a pressure sensitive adhesive thereon and a support layer attached to the non adhesive surface of the backing layer. The dressing is characterised in having an additional edge strip component on the adhesive surface to facilitate application of the dressing to the skin. A removable protector covers the adhesive layer and extends beyond the backing layer. The removable protector may be divided into two or more pieces, of which the smaller one may be folded into a V-shaped handle.

European Patent Application No. EP 0 630 629 describes a hydrogel wound dressing product which includes a thin film layer, an adhesive layer, a backing layer which may be porous, an optional support layer, an optional release liner, and a hydrogel material. The wound may also include a removable tap interposed between the thin film layer and release liner, providing a grip surface for the removal of the release liner from the transparent thin film layer and to facilitate the handling of said wound dressing during application of the dressing to the wound.

A problem associated with the state of the art dressings provided with V-shaped tab members in order to provide a "non-touch" grip for applying the dressing comprising an adhesive layer and a release liner to the skin is that a wide area with an undesired air channel is created in front of the edge of the tab member being positioned across the dressing.

The wide area with an air channel is created partly during manufacturing of a dressing product having an incorporated V-shaped tab member and partly during storage. When manufacturing the V-shaped tab member by bending the area of the bending zone is subjected external forces which will give rise to an internal stress-situation in said area. Prior art V-shaped tab members being bent is seen to have a certain amount of stored stresses. The outer tip of the fold will be influenced by tensile stresses, and the inner tip of the fold will be influenced by compressive stresses. Together these stresses will force the two flaps of the V-shaped tab member from one another, once the dressing product is produced and stored. This spreading effect of the flaps may cause the area of the adhesive layer to detach along the line of bending of the two flaps from the release layer, enabling air to enter between the two said layers and turning the area into an unwanted air channel.

A further problem in conventional V-shaped tab members is that the tensile stresses in the outer tip of the fold and the compressive stresses in the inner tip of the fold makes the thickness of the folded area huge. When manufacturing a dressing, especially when manufacturing a dressing having a thin layer of adhesive, this huge fold with a huge thickness will create a stepwise change of the thickness in the adhesive material, because the adhesive material will be forced to flow to each side of the line of bending of the two flaps, resulting in a local reduced thickness of the adhesive layer. This tendency is even more outspoken when the dressing during manufacturing is subjected pressure in order to obtain bevelled edges along the periphery.

The presence of the wide area with the air channel is followed by a numerous inconveniences. The adhesiveness of the adhesive layer is generally known to be reduced when the adhesive layer is exposed to air. During manufacture, the edges of a dressing are often bevelled in a process applying pressure and optionally heat. When performing this bevelling process on a conventional dressing with a wide area with the air channel, the adhesiveness of the area with the air channel have been seen to be remarkably reduced. This reduction is probably caused by accelerated oxidation due to the heat, but may also be affected by aqueous vapor, small fibres and dust in general present in the surroundings.

Further, the air channel allows more aqueous vapor and dust, e.g. from printed instructions being present in the package to come into contact with the adhesive layer during storage. It is a known and used feature in wound dressing technology that liquids, e.g., wound exudate will reduce the adhesiveness of the adhesive layer during use of the dressing. But, having a wide area with reduced adhesiveness on a fresh dressing will cause problems with the adhesive when applying it.

When applying a dressing having a wide area with an air channel on a patient's skin the dressing will have a tendency to detach. This can cause a serious problem in case of open wounds where the imperviousness of the dressing is important because of the risk of infecting the wound. A dressing having a wide area with a channel of air could form a weak point for a leakage of exudate in case of a suppurating wound.

In case of a dressing having a very thin layer of adhesive the problem of a stepwise change of the thickness creating a locally reduced thickness is even more pronounced. The problem of the area with the air channel is especially serious in case of small dressings, e.g., for blisters or corns because the fraction of area covered by the air channel compared to the remains of the dressing is greater for these small dressings. In this case the dressing could loose the grip after a shorter period of time.

BRIEF SUMMARY OF THE INVENTION

The object of the invention is thus to provide a tab member ensuring an easy handling of a dressing, and in which the problem of a wide area with an air channel is avoided.

The present invention relates to a tab member especially for use as a "non-touch" grip for applying a dressing comprising an adhesive layer and optionally a release liner to skin without touching the adhesive surface of the dressing which is to come into contact with the skin, wherein said tab member comprises at least a first flap member and a second flap member being an integral bent unit or being joined along one edge thereof so as to form a tab having a V-formed cross-section.

Furthermore the invention relates to a method for manufacturing a V-shaped tab member by folding a continuous band of a tab material, and then subjecting the folded area to heat and pressure.

Still further, the invention relates to a method for manufacturing a V-shaped tab member by placing at least two continuous bands of tab material on top of each other, and then subjecting the edges to be joined to heat and pressure.

Finally the invention relates to dressing products incorporating the V-shaped tab member.

BRIEF DESCRIPTION OF THE DRAWINGS

The invention is explained in detail below with reference to the drawings, in which.

DETAILED DESCRIPTION OF THE INVENTION

Figure 1:
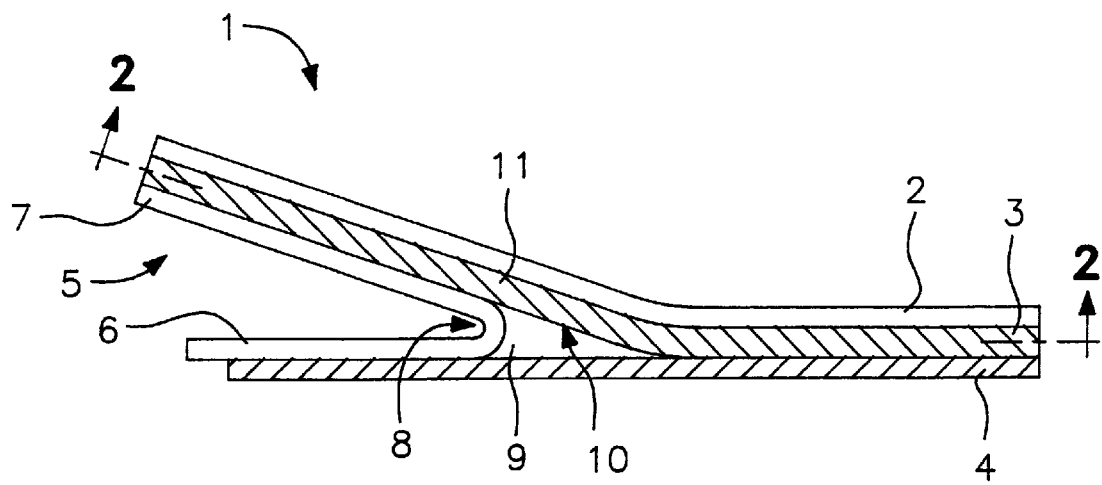
FIG. 1 is a sectional view of an wound dressing having a conventional V-shaped tab member according to the prior art.

The tab member according to the invention is characterized in that the combined thickness of the two flap members in the area of bending or conjunction is smaller than the thickness of a bent edge of the two flap members. This is particularly advantageous as a decrease of the thickness of the area of bending or conjunction results in a decrease of the area of the adhesive in front of the area of bending or conjunction, which may be subjected to air. When decreasing this area the above problems are diminished considerably.

According to a preferred embodiment of the invention the two flap members may constitute one integral bent sheet. In practice, this embodiment is particularly easy to manufacture.

According to another embodiment of the invention the two flap members may be joined along an edge. In practice, this embodiment renders it possible to use different materials for the two flap members. This is advantageous in a dressing, in which the material of the flap in contact with the adhesive layer should have different characteristics than the material of the flap in contact with the release layer.

The thickness of the two flap members may be the same or optionally they may have different thicknesses.

Moreover, according to yet another embodiment of the invention the two flap members may be mutually displaced. In this way the stepwise change of the thickness will be further minimized.

It is preferred that the V-shaped tab member of the invention is made from one or more materials being easily removed from the adhesive of the dressing and the release liner, preferably one or more materials selected from the group of thermoplastic olefins. Common for all the materials used as V-shaped tab members is that they are preferably siliconised or treated in another way in order to secure an easy release from the adhesive.

In a second aspect, the invention relates to a method for manufacturing a V-shaped tab member, especially for use as a "non-touch" grip for applying a wound dressing comprising an adhesive layer and optionally a release liner to the skin, wherein said tab member comprises at least a first flap member and a second flap member being joined along one edge thereof so as to form a tab having a V-formed cross-section substantially perpendicular to the line of folding, characterised in that a continuous band of a tab material is folded, after which the folded area is subjected to pressure in order to reduce the total thickness of the two flap members in the folded area as compared to the thickness of a fold not subjected to pressure.

It is preferred to reduce the total thickness of the two flap members in the folded area by passing the continuous band of folded material through a pair of optimally heated rollers, after which the continuous V-shaped band optionally can be cut into appropriate sizes forming the tab members. The temperature of such rollers will depend on the material and the environmental temperature. It is advantageous when the folded area is subjected to heat separately before being subjected to pressure giving the opportunity of a better temperature control.

In a third aspect, the invention relates to a method for manufacturing a V-shaped tab member, especially for use as a "non-touch" grip for applying a wound dressing comprising an adhesive layer and optionally a release liner on a wound, wherein said tab member comprises at least a first flap member and a second flap member being joined along one edge thereof so as to form a tab having a V-formed cross-section substantially perpendicular to the line of conjunction, characterized in that, at least two continuous bands of tab material are placed on top of each other having the edges to be joined aligned, after which the edges are joined by the action of heat and pressure.

It is preferred to join the edges by sealing and to use a pair of rollers to press the sealed edges, whereafter the continuous V-shaped sheetband optionally can be cut into appropriate sizes forming the tab members.

In accordance with another aspect of the invention the edges are joined by gluing before being subjected to pressure.

Instead of using a pair of rollers it is possible to use a system of more rollers or to use another mechanical device, e.g., a heated press.

The heating of a continuous band could be done at the same time as the pressing is performed. This could be done by a pair of heated rollers.

The either one or two continuous bands of a film material might in another method for manufacturing the V-shaped tab member be passed through a stamping and sealing apparatus. Instead the conjunction forming a straight line, it could alternatively form a series of cyclic curves, repeating for each dressing. The band could optionally still be continuous after the stamping, by the open edges of the V-shaped member. Further a V-shaped tab member according to this invention can also be used together with other products including adhesive surfaces, e.g., ostomy products and adhesive strips for mastectomy products as well as industrial adhesive strips.

In a further aspect, the invention relates to a dressing comprising an adhesive layer and optionally a release liner and a V-shaped tab member for applying a dressing to the skin, characterized in that the tab member comprises at least a first flap member and a second flap member being an integral bent unit or being joined along one edge thereof so as to form a tab having a V-formed cross-section substantially perpendicular to the line of bending or conjunction, and wherein the combined thickness of the two flap members in the area of conjunction is smaller than the thickness of a bended edge of the two flap members.

This combination of a dressing and a V-shaped tab member according to the invention offers a large number of advantages to the patients.

In still a further aspect, the invention relates to a dressing comprising an adhesive layer and optionally a release liner and at least two V-shaped tab members for applying a dressing to the skin, characterized in that each of the tab members comprises at least a first flap member and a second flap member being an integral bent unit or being joined along one edge thereof so as to form a tab having a V-formed cross-section substantially perpendicular to the line of conjunction, and wherein the combined thickness of the two flap members in the area of the bending zone or conjunction is smaller than the thickness of a bended edge or the combined thickness of the two flap members.

The embodiment with two V-shaped tab members having their zones of conjunction in close contact has in practice proved to be particularly advantageous as the second flap members cover the the whole surface of the adhesive layer, therefore the release liner is not necessarily needed and the dressing is much easier to apply.

FIG. 1 illustrates a prior art wound dressing 1 comprising a top film 2, an adhesive layer 3, a protective layer 4 also referred to as the release layer and a conventional V-shaped tab member 5. The flaps 6, 7 of the conventionally used V-shaped tab member 5 tends to spread from one another forming an angle due to the memory of the material in the folded area 8. This spreading tendency results, as described above, in that the adhesive layer 3 will detach the release layer 4 of the dressing 1. As mentioned above this detaching of the adhesive layer 3 will result in the forming of a channel 9 between the adhesive layer 3 and the release layer 4 along the line of bending of the two flaps 6, 7 of the V-shaped tab member 8, as it is illustrated in FIG. 1.

Furthermore the adhesive layer 3 is seen locally to have a reduced thickness at 11. This stepwise change of the thickness is created because the adhesive material in the adhesive layer 3 will be forced to flow to each side of the line of conjunction 8 of the two flaps 6, 7. This is even worse when the dressing product includes bevelled edges along the periphery.

Figure 2:
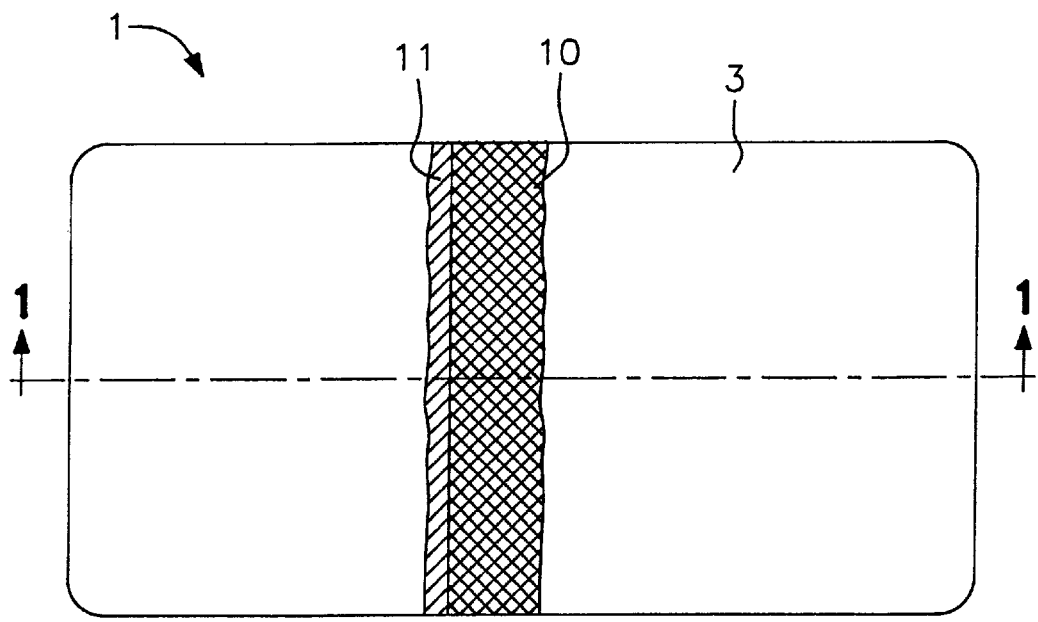
FIG. 2 illustrates a view from below, of the wound dressing in FIG. 1, where the release layer and the V-shaped tab member have been removed.

As it can be seen clearly from FIG. 2 showing the prior art dressing 1 according to FIG. 1 seen from below, after removing the release layer 4 and the V-shaped tab member 5, an unwanted channel 9 is present across the dressing 1. In FIG. 2 the adhesive layer 3 is shown with the area 11 influenced by the differences of the thickness, and the area 10 influenced by the air channel. The channel 9 will immediately be filled with air, which will lower the adhesiveness of the adhesive layer 3 in the area 10 giving rise to a numerous inconveniences as stated above.

Figure 3:
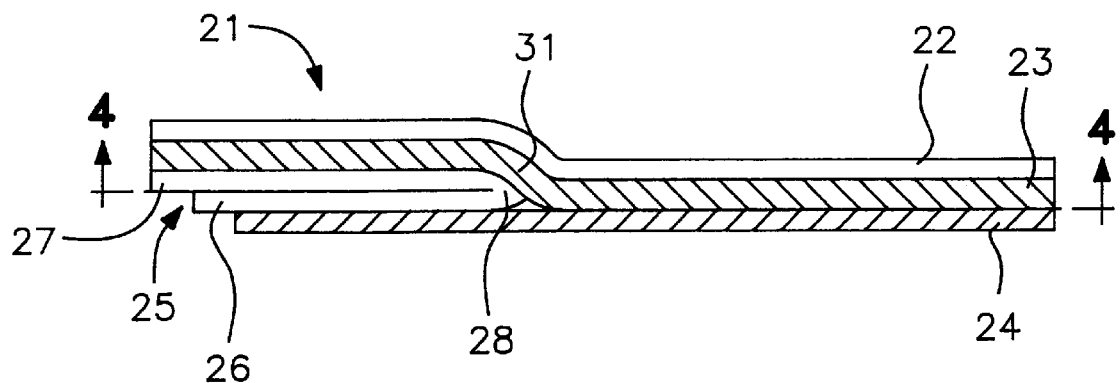
FIG. 3 illustrates a sectional view of a wound dressing having a V-shaped tab member according to an embodiment of the invention.

FIG. 3 illustrates a dressing 21 according to the invention comprising a top film 22, an adhesive layer 23, a protective layer 24 also referred to as the release liner and a V-shaped tab member 25 according to the invention. The dressing may further comprise a protective layer on top of the top film. The flaps 26, 27 of the V-shaped tab member 25 no longer tend to spread from one another.

Figure 4:
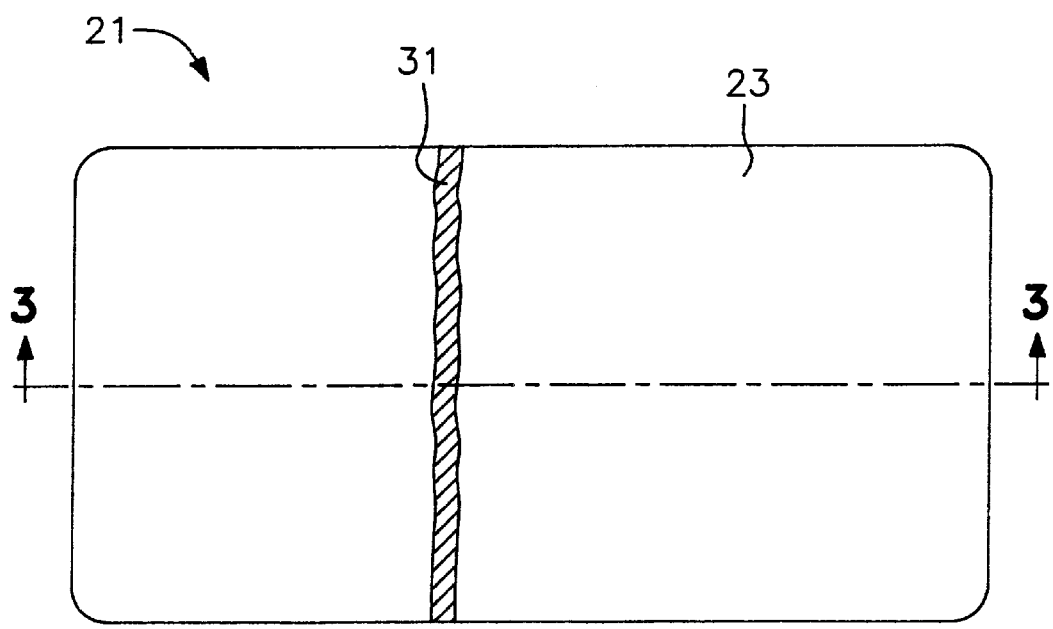
FIG. 4 illustrates a view from below of the wound dressing of FIG. 3, where the release layer and the V-shaped tab member have been removed.
Figure 5:
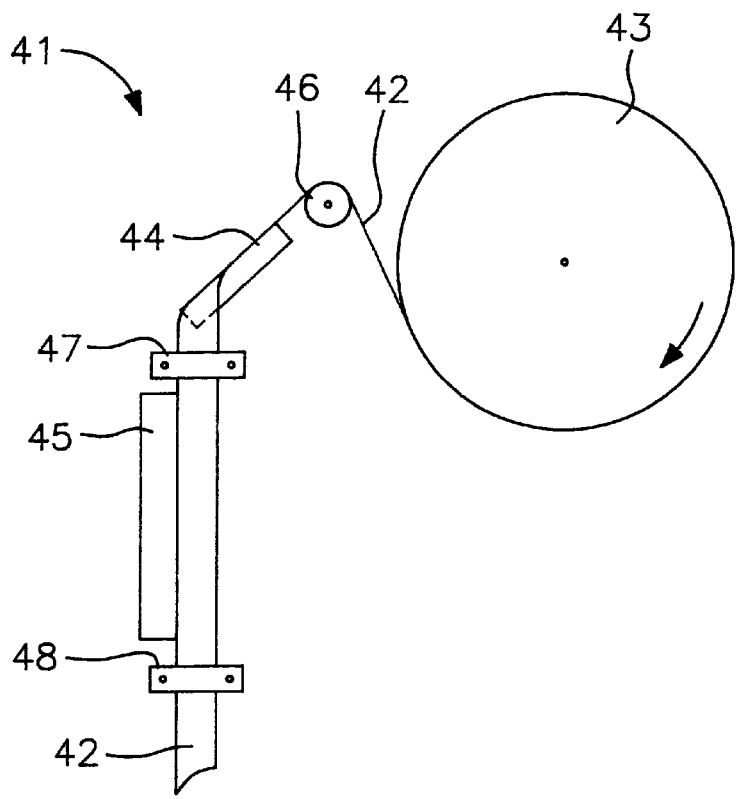
FIGS. 5 and 6 illustrate schematically an example of a method for manufacturing a continuous band of V-shaped tab members.

During manufacturing of the novel V-shaped tab member 25 of the invention from the continuous band 42, shown on FIG. 5, the stored stresses have been relaxed. The adhesive layer 23 will hardly detach from the release liner 24 of the dressing 21 and there is, as shown in FIG. 4, no channel formed between the adhesive layer 23 and the release liner 24 in the area 31 along the line of conjunction 28 of the two flaps 26, 27 of the V-shaped tab member 25. The thickness of the area 31 of folding 28 of the tab member 25 has been diminished considerably, resulting in a reduced stepwise change of the thickness. The adhesive material in the adhesive layer 23 has almost no tendency to flow to each side of the area of bending 28 of the V-shaped tab member 25 during manufacture.

According to the invention the V-shaped tab member 25 is made from a material such as paper, metal, and/or a polymer. E.g. a polyolefin such as polyethylene, polypropylene or polybutylene, preferable a high density polyethylene (HDPE) which may be siliconized on one side (e.g., HDPE no.1710) or laminated with silicone (e.g., HDPE no.1800), polyethyleneterepthalate and polyethylene (PETP/PE), in a combination of two flaps of different material (PETP/PE) was used together with (PETP), cast polypropylene film (e.g. PP no.1015), siliconized cast polypropylene film (e.g. PP no. 1803), or polyesters such as (e.g., PETP no. 1019), polyester (e.g., PETP no. 1019), or siliconised polyester (e.g. PETP no. 1803). The numbers are referring to Europhan numbers.

In a preferred embodiment of the invention, the material may be siliconized, on either one or both sides or treated in a similarly way in order to achieve the removal of the tab member from the adhesive layer.

The material preferably has a thickness ranging from a few microns to a millimeter. Especially material thickness' in the area of 30–60, preferably 36, microns have proved to be effective.

Figure 6:
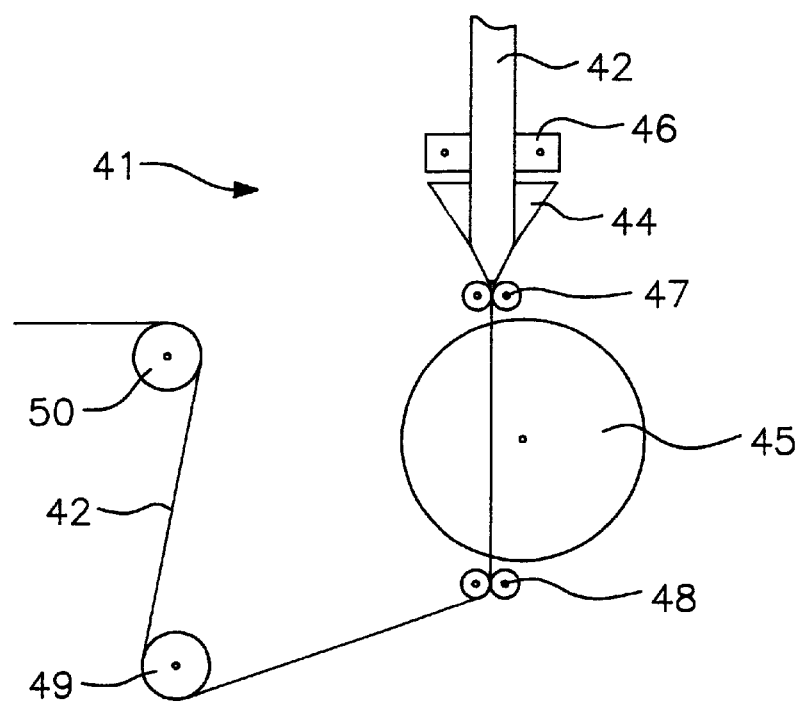

FIGS. 5 and 6 illustrate schematically an apparatus 41 for manufacturing a continuous band 42 is of V-shaped tab members 25. A continuous band 42 wound up on a roll 43, and guided over a roller 46 with the purpose of contacting a bended plate 44. By contacting the bended plate the band is folded in longitudinal direction, whereafter the band passes through a first pair of rollers 47, which 15 applies pressure to the fold. After the band 42 has passed the first pair of rollers 47 the outer tip of the fold further passes a heating device, e.g., a heated plate 45. While passing the heated plate 45 the material of the band 42 is heated to a temperature lying above the softening temperature of the material. The folded area of the band then passes through a second pair of rollers 48 applying pressure to the fold. Further the folded band 42 is guided over some reeling rollers 49, 50. Finally the continuous and folded band is optional reeled up on a roll or directly used.

Figure 7:
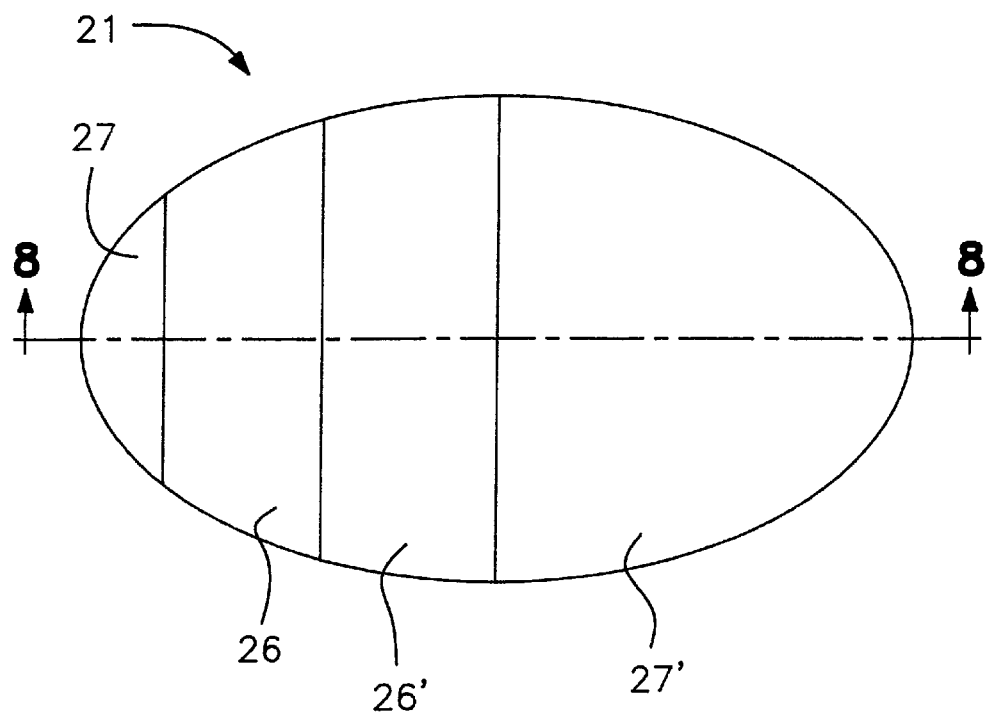
FIG. 7 illustrates from below a wound dressing having two V-shaped tab members according to another embodiment of the invention.
Figure 8:
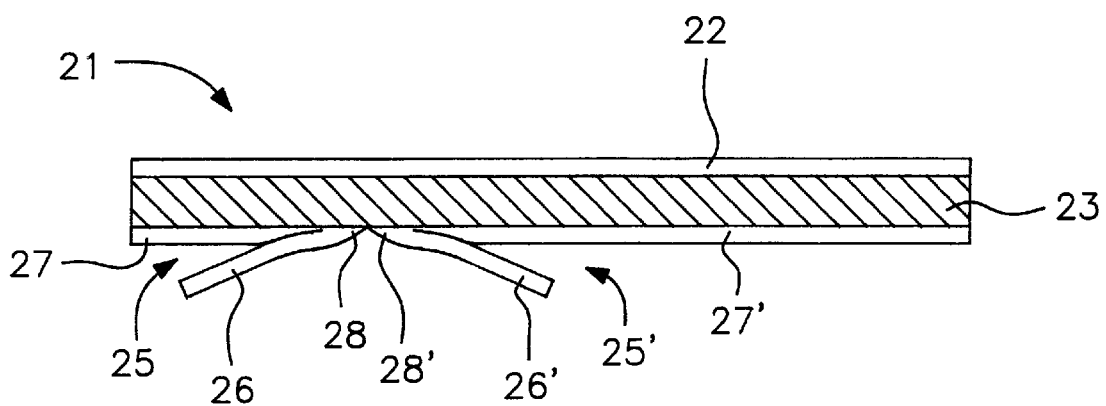
FIG. 8 illustrates a sectional view of the wound dressing of FIG. 7.

FIGS. 7 and 8 illustrates a dressing 21 according to the invention comprising a top-film 22, an adhesive layer 23 and two V-shaped tab members 25, 25' according to the invention. The dressing may further comprise a not shown protective layer on top of the top film. The flaps 26, 26', 27, 27' of the V-shaped tab members 25, 25' no longer tend to spread from one another close to the line of conjunction.

During manufacturing of the novel V-shaped tab members 25,25' of the invention from a continuous band 42, shown on FIG. 5, the stored stresses have been relaxed.

There is, as shown in FIG. 8, no channel formed between the adhesive layer 23 and the two V-shaped tab members 25, 25' along the line of conjunction 28, 28' of the two flaps 26, 26', 27, 27' of each of the V-shaped tab members 25, 25'. The thickness of the area of folding 28, 28' of the tab member 25, 25' has been diminished considerably, resulting in a reduced stepwise change of the thickness. The adhesive material in the adhesive layer 23 shows almost no tendency to flow to each side of the area of bending 28, 28' of the V-shaped tab members 25, 25' during manufacture.

The V-shaped tab members 25, 25' are shown having different sizes. They may as well be formed having the same size. The flaps 26, 26' in FIGS. 7 and 8 are smaller than the flaps 27, 27'. The flaps 26, 26' could as well be as long as the flaps 27, 27', or one of the flaps 26, 26' or both of the flaps 26, 26' could be longer than the flaps 27,27', within the scope of the invention.

MATERIALS AND METHODS
EXPERIMENTAL PART

The invention is explained more in detail below with reference to the Examples disclosing embodiments of the present invention. The examples are not considered to be limiting to the scope of the invention which is defined in the appended claims.

EXAMPLE 1

Preparation of a V-shaped tab member according to the invention by folding, heating and rolling.

A roll with a continuous band of siliconized polyethylene (PETP no. 1803) with a thickness of 36 microns was placed in the apparatus of the type shown in FIGS. 5 and 6, so that the siliconised side faced upward when reeling off the band. The continuous band is guided over a roll with the purpose of contacting a bended plate made from stainless steel. By contacting the bended plate, the band is folded longitudinally with the siliconized side being outward, whereafter the band passes through a first pair of rollers, which applies pressure to the fold. After the band has passed the first pair of rolls the outer tip of the fold further passes over a heated, teflon coated plate. The temperature of the teflon coated plate is between 120° and 200° C. While sliding down the heated plate the material of the band is heated to a temperature lying above the softening temperature of the material. The folded band then passes through a second pair of rollers applying pressure to the fold and thereby deforming that folded area. Further the folded band is guided over some reeling rollers. Finally the continuous and folded band is optional wound up on a roll or directly used.

EXAMPLE 2

Preparation of a V-shaped tab member according to the invention by sealing and subjecting pressure.

A sheet of continuous siliconized polyester (PETP no. 1803) with a thickness of 36 microns was placed on top of another sheet of the same continuous siliconized polyester (PETP no.1803). One edge of the two sheets was lead into an Elwis impulse sealing apparatus (Elwis Pack A/S) having a sealing strip on both jaws and teflon material on top of the sealing strips. The two polyester bands were heated and sealed together along an edge using a sealing time setting of 3,1 and a cooling time setting of 4. The apparatus also applied pressure to the sealed area as to simulate a pair of rollers. After cooling the continuous sheet of V-shaped tab member was cut into pieces of appropriate size.

EXAMPLE 3

Preparation of a V-shaped tab member according to the invention from two different materials by sealing and subjecting pressure.

A sheet of Wipak® (Wihuri Oy Wipak) laminated sterile packaging paper with a thickness of 100 microns was placed on top of a sheet of siliconized continuous polyester (PETP/PE no. 1803) with a thickness of 36 microns. The edge of the Wipak® sterile packaging paper being displaced 0.5 mm from the edge of the polyester. The edges of the sheets were placed in an Elwis impulse sealing apparatus (Elwis Pack A/S). The sealing apparatus having sealing strips on both jaws, and teflon material on top of the sealing strips. The two polyester sheets were heated and sealed together by using a sealing time setting of 3,2 and a cooling time setting of 4. The apparatus also applied pressure to the sealed area as to simulate a pair of rollers. After cooling the continuous band of V-shaped tab member was cut into pieces of appropriate size.

EXAMPLE 4

Preparation of a V-shaped tab member according to the invention from sheets with different thickness' by sealing and subjecting pressure.

A sheet of continuous polyester (PETP/PE) with a thickness of 47 microns was placed on top of a sheet of continuous siliconized polyester (PETP) with a thickness of 36 microns. The edges of the two sheets were placed in an Elwis impulse sealing apparatus (Elwis Pack A/S). The two polyester sheets were heated and sealed together by using a sealing time setting of 3 and a cooling time setting of 4.

The invention has been described with reference to examples of specific embodiments thereof. Many modifications can be carried out without thereby deviating from the scope of the invention being defined by the scope of the appended claims.

What is claimed is:

1. A tab member (25), especially for use as a "non-touch" grip for applying a dressing (21) comprising an adhesive layer (23) to a wound or skin without touching a surface of the adhesive, wherein said tab member (25) comprises at least a first flap member (26) and a second flap member (27), wherein the tab member is an integral bent unit or is joined along one edge thereof so as to form a tab (25) having a V-shaped cross-section substantially perpendicular to a line of bending or conjunction, the thickness of the V-shaped tab member is 30–60 microns and the combined thickness of the two flap members in the area of bending or conjunction (28) is has a heat and pressure reduced thickness smaller than the thickness of a bent edge or the combined thickness of the two flap members.

2. The V-shaped tab member (25) as claimed in claim 1, comprising two flap members (26, 27), characterised in that wherein the two flap members (26, 27) constitute one integral bended sheet.

3. The V-shaped tab member (25) as claimed in claim 1, wherein the two flap members (26, 27) are joined along an edge.

4. The tab member (25) as claimed in claim 3, wherein the thickness of the two flap members (26, 27) are the same.

5. The member (25) as claimed in claim 1 wherein the two member comprises one or more materials treated to be easily removable from the adhesive (23) of the dressing (21) and the release liner (24).

6. The tab member (25) as claimed in claim 5, wherein the one or more materials are thermoplastic olefins.

7. The tab member (25) as claimed in claim 1, wherein the dressing (21) further comprises a release liner (24).

8. A method for manufacturing a V-shaped tab member (25), especially for use as a "non-touch" grip for applying a dressing (21) comprising an adhesive layer (23) to a wound or skin, wherein said tab member (25) comprises at least a first flap member (26) and a second flap member (27) joined along one edge thereof to form a tab having a V-shaped cross-section substantially perpendicular to a line of bending, comprising folding a continuous band (42) of a tab member material and thereafter subjecting the folded area to heat and pressure to reduce a total thickness of the two flap members (26, 27) in the fold as compared to the thickness of a bent edge of the two flap members (26, 27).

9. A method as claimed in claim 8, wherein the thickness is reduced by a pair of rollers (47, 48).

10. The method as claimed in claim 9, wherein the V-shaped band is cut into an appropriate size forming the tab member (25).

11. The tab member (25) as claimed in claim 8, wherein the dressing (21) further comprises a release liner (24).

12. A method for manufacturing a V-shaped tab member (25), especially for use as a "non-touch" grip for applying a dressing (21) comprising an adhesive layer (23) to a wound or skin, wherein said tab member (25) comprises at least a first flap member (26) and a second flap member (27) joined along one edge thereof to form a tab having a V-shaped cross-section substantially perpendicular to a line of bending or conjunction comprising placing at least two continuous bands of tab material on top of each other with the edges to be joined aligned and thereafter joining the edges by the action of heat and pressure.

13. A method as claimed in claim 12, wherein the edges are sealed together and pressed by way of a pair of rollers after which the continuous V-shaped sheetband is optionally cut into appropriate sizes forming the tab.

14. The tab member (25) as claimed in claim 13, wherein the dressing (21) further comprises a release liner (24).

15. The method as claimed in claim 13, wherein the edges are sealed together and pressed by a pair of rollers and the V-shaped band is cut into an appropriate size forming the tab member (25).

16. The tab member (25) as claimed in claim 12, wherein the dressing (21) further comprises a release liner (24).

17. A dressing (21) comprising an adhesive layer (23) and at least one V-shaped grip tab member (25) for applying a dressing (21) to a wound or skin, wherein said tab member (25) comprises at least a first flap member (26) and a second flap member (27), wherein the tab member is an integral bent unit or is joined along one edge thereof to form a tab having a V-shaped cross-section substantially perpendicular to a line of bending or conjunction, the thickness of the V-shaped tab member is 30–60 microns and the combined thickness of the two flap members in the area of the bending or conjunction has a heat and pressure reduced thickness smaller than the thickness of a bent edge or the combined thickness of the two flap members.

* * * * *